(12) United States Patent
Liang et al.

(10) Patent No.: US 6,182,016 B1
(45) Date of Patent: *Jan. 30, 2001

(54) MOLECULAR CLASSIFICATION FOR PROPERTY PREDICTION

(76) Inventors: Jie Liang, Apt. F307 927 Parkview Dr., King of Prussia, PA (US) 19406; Herbert Edelsbrunner, 2003 Trout Valley Rd., Champaign, IL (US) 61821

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/918,624

(22) Filed: Aug. 22, 1997

(51) Int. Cl.$^7$ ................................................. G01N 33/50
(52) U.S. Cl. ............................ 702/22; 702/21; 702/27; 702/30
(58) Field of Search ................................ 702/27, 28, 29, 702/30, 31, 32, 4–22; 345/419, 425

(56) References Cited

U.S. PATENT DOCUMENTS

| | | |
|---|---|---|
| 4,642,762 | 2/1987 | Fisanick . |
| 5,418,944 | 5/1995 | DiPace et al. . |
| 5,463,564 * | 10/1995 | Agrafiotis et al. ............. 702/31 |
| 5,500,807 * | 3/1996 | Lavin et al. .................. 702/22 |
| 5,577,239 | 11/1996 | Moore et al. . |
| 5,850,229 * | 12/1998 | Edelsbrunner et al. .......... 345/425 |

OTHER PUBLICATIONS

Edelsbrunner et al., Algorithmica, vol. 15, pp. 223–241 (1996).

Edelsbrunner et al., IEEE Proceedings of the 28th Annual Hawaii International Conference on System Sciences, pp. 256–264 (1995).

H. Edelsbrunner, Discrete Comput. Geom., vol. 13, pp. 415–440 (1995).

Michael A. Facello, Computer Aided Geometric Design, vol. 12, pp. 349–370 (1995).

Good et al., Journal of Computer–Aided Molecular Design, vol. 9, pp. 373–379 (1995).

Good et al., Journal of Computer–Aided Molecular Design, vol. 9, pp. 1–12 (1995).

Good et al., Three Dimensional Structure Database Searches, Chapter 2, Reviews in Computational Chem., vol. 7, pp. 67–117 (1996) Lipkowitz and Boyd, Editors.

Rajan et al., Discrete Comput. Geom., vol. 12, pp. 189–202 (1994).

Sharma et al., J. Chem. Inf. Comput. Sci., vol. 37, pp. 273–282 (1997).

Sheridan et al., J. Chem. Inf. Comput. Sci., vol. 36, pp. 128–136 (1996).

Singh et al., Journal of Computational Biology, vol. 3, No. 2, pp. 213–221 (1996).

* cited by examiner

*Primary Examiner*—Kamini Shah
*Assistant Examiner*—Bryan Bui
(74) *Attorney, Agent, or Firm*—Westerman, Champlin & Kelly, P.A.; Peter S. Dardi

(57) ABSTRACT

A molecular classification method is based on a space filling description of a molecule. The three dimensional body corresponding to the space filling molecular structure is divided into Voronoi regions to provide a basis for efficiently processing local structural information. A Delaunay triangulation provides a basis for systematically processing information relating to the Voronoi regions into shape descriptors in the form of topological elements. Preferably, additional shape and/or property descriptors are included in the classification method. The classification methods generally are used to identify similarities between molecules that can be used as property predictors for a variety of applications. Generally, the property predictions are the basis for selection of compounds for incorporation into efficacy evaluations.

20 Claims, 8 Drawing Sheets

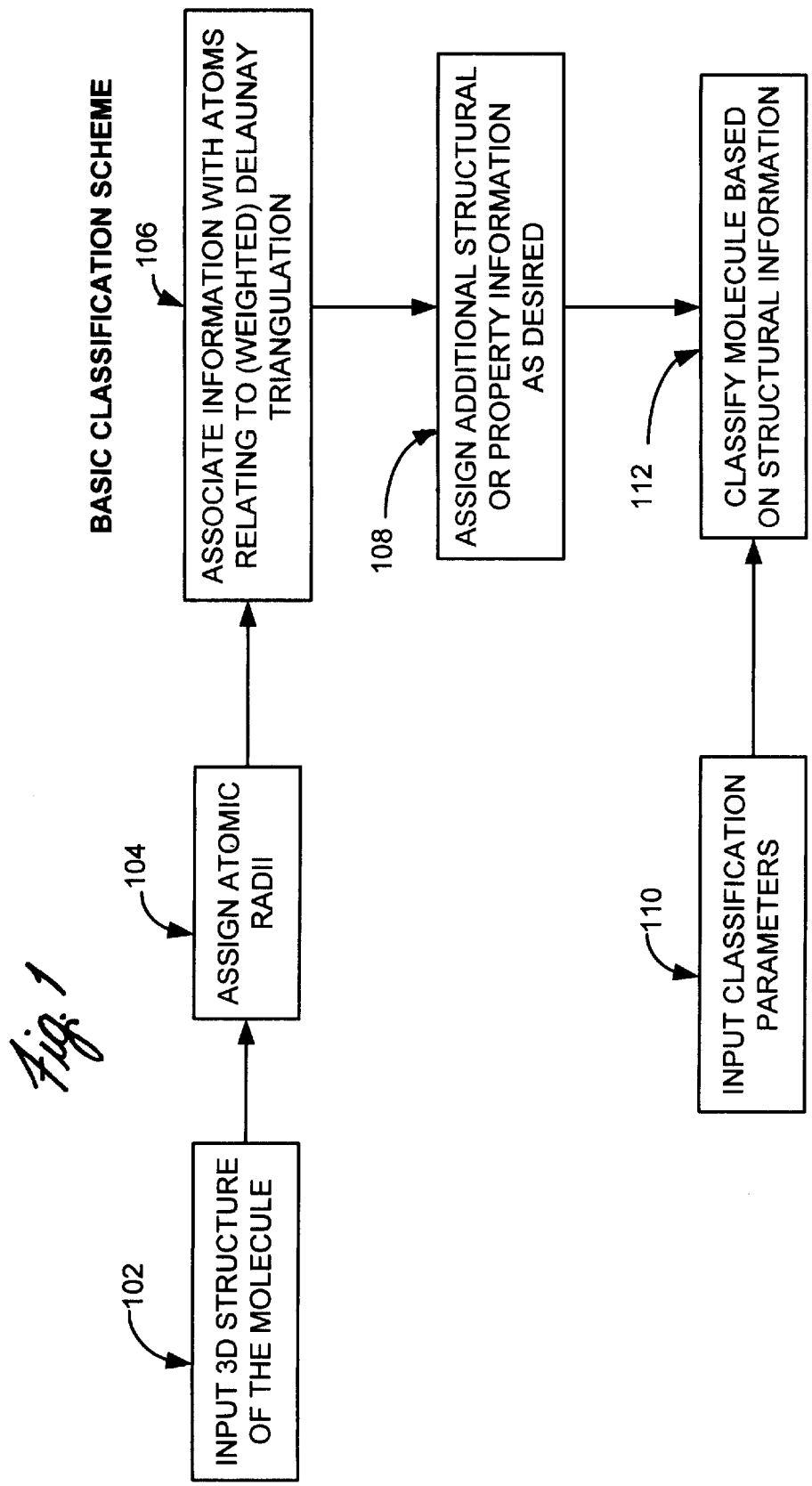

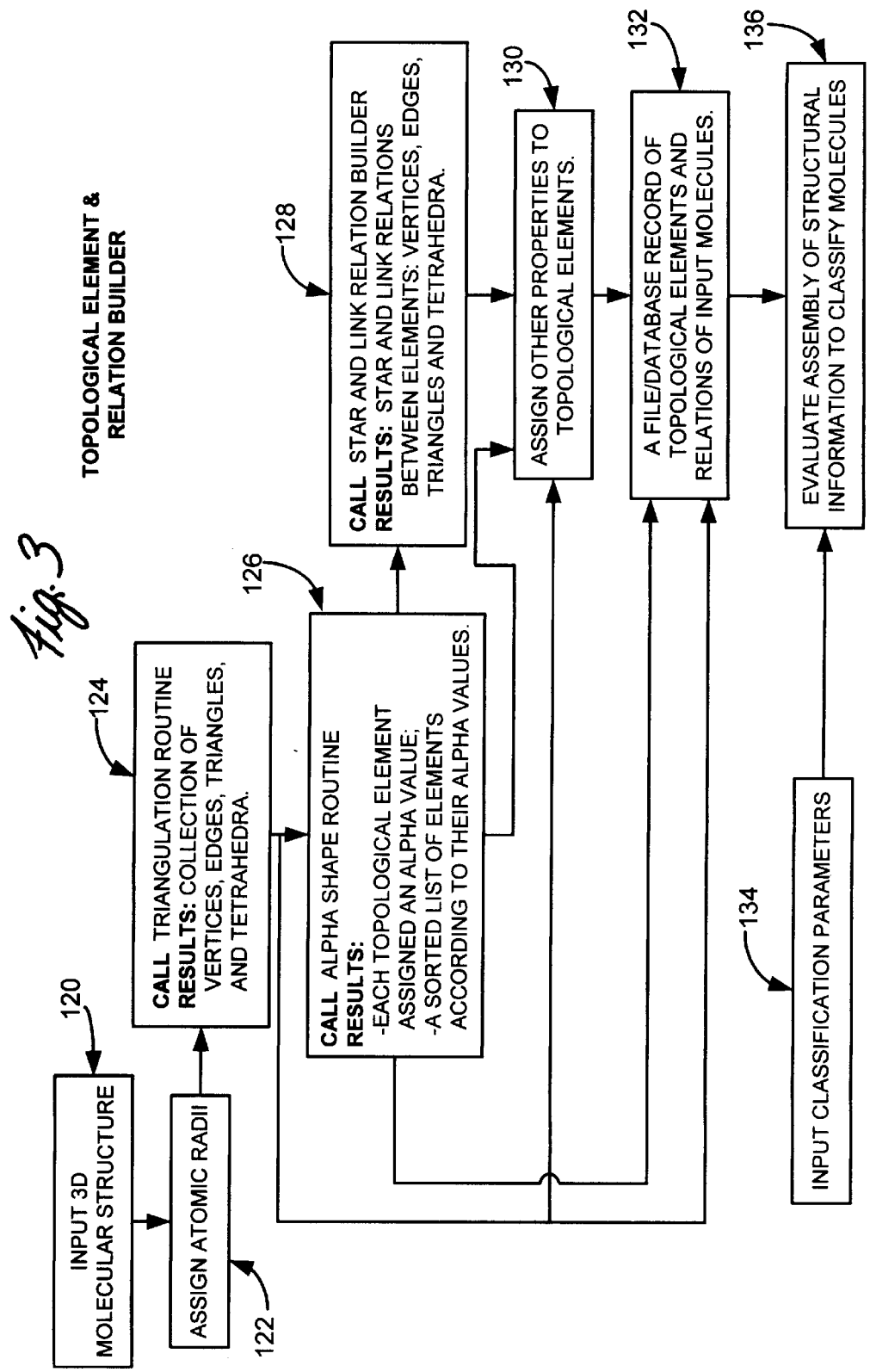

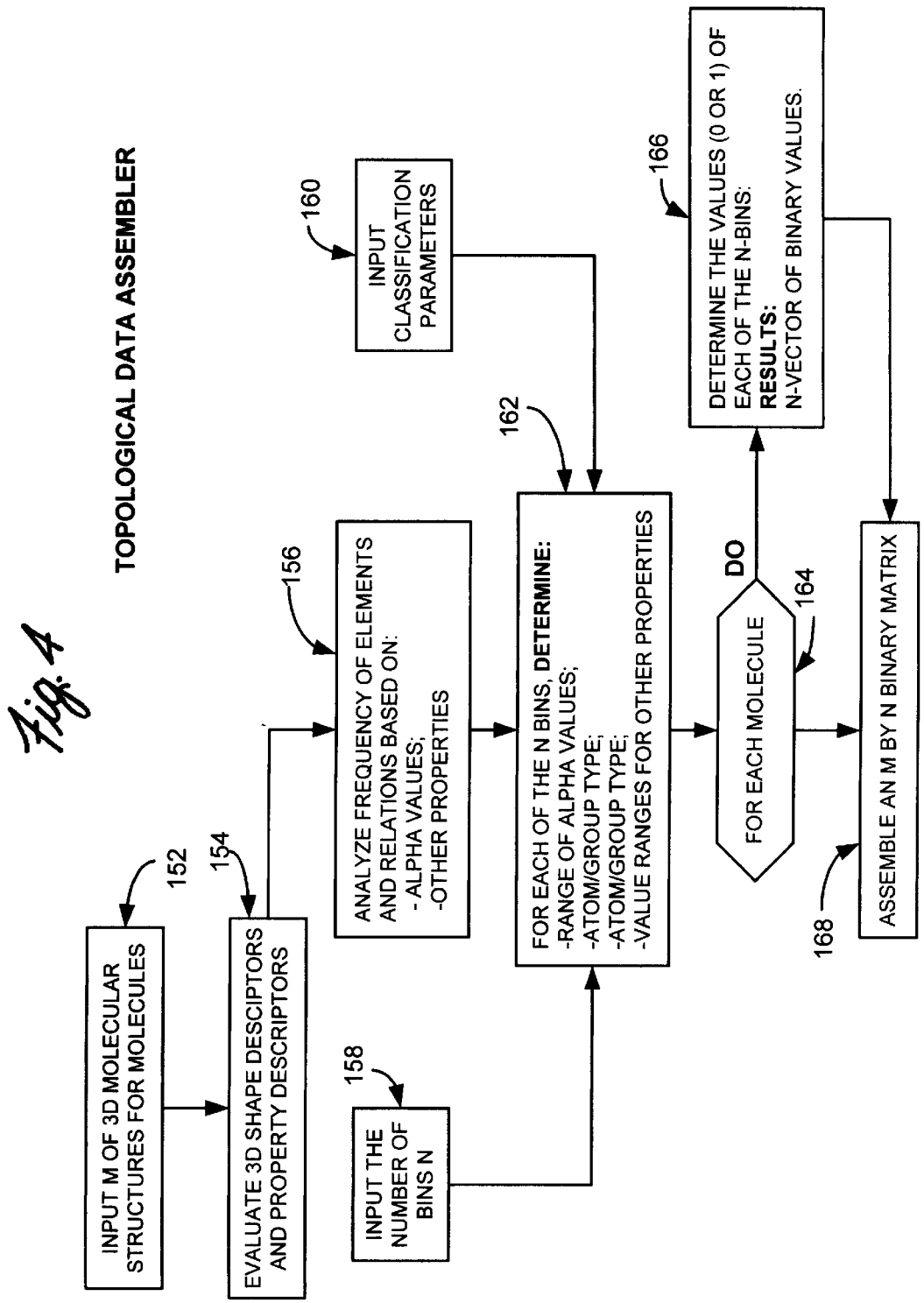

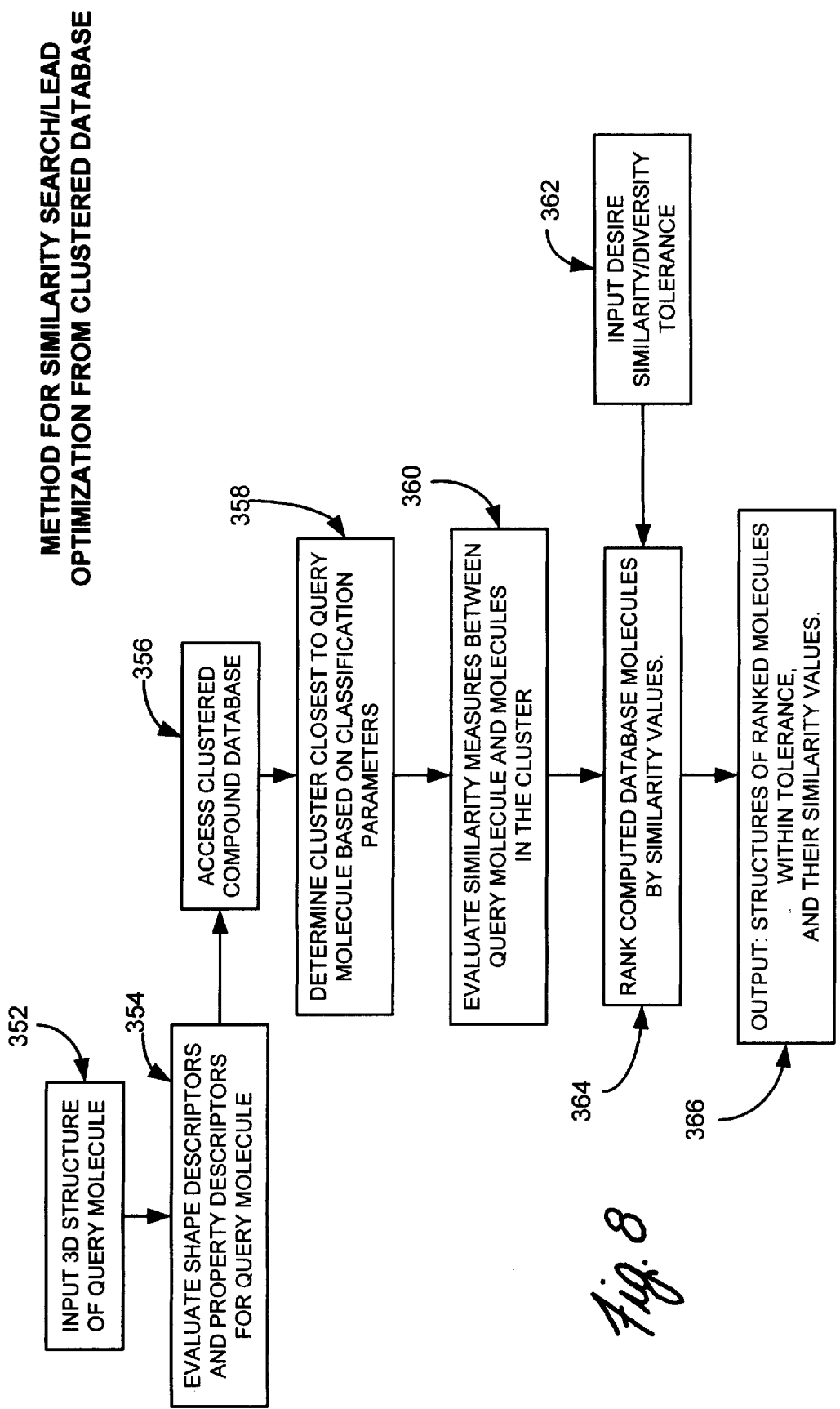

MOLECULAR CLASSIFICATION FOR PROPERTY PREDICTION

FIELD OF THE INVENTION

The invention relates to molecular classification approaches useful to generate comparisons that can be applied to combinatorial chemistry applications or other applications where the determination of similarities and differences of molecules is desirable.

BACKGROUND OF THE INVENTION

The selection of useful chemical compounds for any application can be a time consuming and expensive task. Typically, the first step is to look for signs of the desired activity in any compound available. The compounds can be natural or synthetic. Starting from a promising compound, the compound can then be modified, traditionally through one-at-a-time modifications to the structure. In the drug industry, for example, many years and hundreds of millions of dollars may be required to bring a drug to market. Therefore, attempts have been made to make the process more efficient.

More systematic approaches, generally termed combinatorial chemistry, are based on having combinatorial collections or libraries of compounds that can be screened for activity. A library can be constructed based on general chemical principles. The library is then input into a systematic development process. Examples of systematic development processes include a parallel synthesis approach and a split-and-mix synthesis approach.

In the parallel synthesis approach, the building blocks for a study are placed in separate reaction vessels, generally wells of a microtitre plate. The appropriate syntheses can be carried out in each well to produce a set of products. These can then be used in efficacy screening, toxicity studies, and the like. Efficacy screening can involve tests for biological activity or any other chemical property.

In a split-and-mix synthesis, a series of first reactants are attached to polystyrene beads. These attached reactants are mixed together and split into a series of vessels, tubes or wells. A different second reactant is added to each vessel. If a third reactant is involved, the second group is again mixed together and split. A different third reactant is added to the tubes containing the second mixtures. The most potent of the final mixtures are determined. A variety of techniques can be used to ascertain the most potent combination.

While drug design is a significant application of these techniques, these combinatorial chemistry approaches can be used for the production of chemicals for any application. For example, they have also been used to identify high temperature superconductors, liquid crystals for flat panel displays, and materials for constructing batteries. The assays incorporated into the techniques are appropriate for the type of compound desired. Basic to the application of these development programs is the construction of a suitable library of chemicals.

SUMMARY OF THE INVENTION

The present methods provide an accurate and efficient approach for computing three-dimensional descriptors for three-dimensional substructure searching, similarity searching, combinatorial chemistry library design and for diversity management. Molecular descriptors are of central importance for developing high throughput screening, especially for drug lead searching and drug lead optimization.

The present approach is based on geometrical constructs that provide detailed local structural information along with relationships between the neighboring local structures. An efficient and systematic characterization can be performed based on the geometrical construction. Considerable versatility is provided to adjust the desired features of the characterization and the important features for comparison between molecules.

In a first aspect, the invention features a method of classifying molecules for assisting with the selection of compounds for further study, the method including the steps of:

(a) forming a 3-dimensional body by placing a potentially overlapping ball around each atom or group of atoms of the molecule, the ball having a a radius selected for the particular type of atom or group of atoms;

(b) generating structural descriptors reflecting information about neighboring atoms or groups of atoms, the structural descriptors relating to the Voronoi diagram corresponding to the 3-dimensional body; and (c) classifying the molecule using the descriptors.

The descriptors can be obtained by performing a weighted Delaunay triangulation to obtain topological elements associated with the molecular structure. The topological elements can be selected from the group consisting of a vertices, edges, triangles, tetrahedrons and combinations thereof.

Furthermore, an additional descriptor can be associated with each atom or group of atoms. The additional descriptor can relate to a property selected from the group consisting of polarity, hydrophobicity, hydrophilicity, chemical reactivity, location relative to the surface of the molecule, location relative to the convex hull of the three-dimensional body, local concavity of the surface of the molecule and relationship to cavities. Alternatively, the additional descriptor can be selected from the group consisting of the characteristic alpha value of the structural descriptors, the star relation or the link relation.

In another aspect, the invention features a method of classifying molecules for assisting with the selection of compounds for further study, the method including the steps of:

(a) performing a Delaunay triangulation based on a 3-dimensional body associated with the structure of the molecule based on the atomic centers to obtain a set of topological elements including, at least, triangles and tetrahedra;

(b) classifying the molecule based on these topological elements.

In another aspect, the invention features a method of identifying molecules that are similar to a known compound comprising the steps of:

(a) classifying the known compound based on a classification system of the invention;

(b) identifying significant elements within the classification scheme in terms of classification parameters;

(c) determining classifications of relevant molecules having the identified classification parameters similar or identical with the known compound; and (d) establishing the structure of a molecule corresponding to the determined classifications of relevant molecules.

The method of identifying molecules that are similar to a known compound can further include the step of evaluating the chemical properties of a chemical compound corresponding to the established structure.

In another aspect, the invention features a method of evaluating the degree of similarity between two molecules comprising the steps of:

(a) classifying the two molecules based on a classification method of the invention; and (b) determining the degree of similarity between the two molecules based on a comparison of the descriptors determined for each of the two molecules.

In another aspect, the invention features a method of selecting a diverse group of compounds for evaluation of efficacy from a collection of relevant molecules, the method including the steps of:

(a) determining a range of classifications for an evaluated set of compounds, using a classification method of the invention;

(b) identifying significant elements within the classification scheme in terms of classification parameters; and (c) selecting based on the classification parameters a diverse set of compounds within the evaluated set of compounds.

In another aspect, the invention features a method of selecting and evaluating the efficacy of a chemical compound, the method including the steps of:

(a) classifying a known compound based on a classification method of the invention;

(b) identifying a compound from a group of compounds having a similar classification, with respect to significant features, to the known compound based on the same classification method used in step (a); and (c) evaluating efficacy of the identified molecule using a chemical or pharmacological test.

The invention further features an electronic storage device including a storage medium, where the storage medium stores a computer program for implementing a classification method of the invention.

BRIEF DESCRIPTION OF THE DRAWINGS

FIG. 1 is a flow chart outlining the basic classification process of the invention.

FIG. 3 is a flow chart outlining a specific embodiment of the classification process.

FIG. 4 is a flow chart outlining a topological data assembler involving classification for a group of molecules.

FIG. 8 is a flow chart outlining a similarity search based on a clustered database.

DESCRIPTION OF THE PREFERRED EMBODIMENTS

Figure 2A:
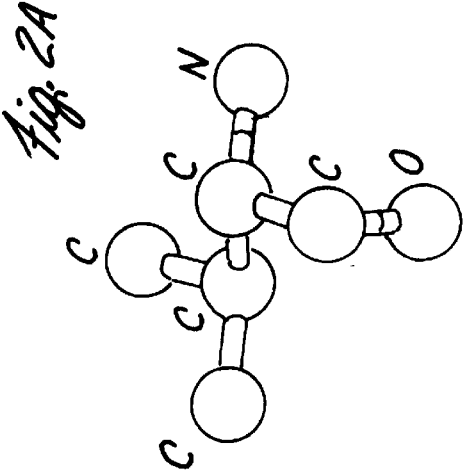
FIG. 2A is a schematic depiction of the molecular structure of the heavy atoms of a valine amino acid fragment.
Figure 2B:
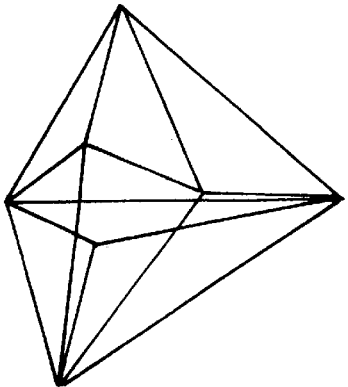
FIG. 2B is a depiction of the bounding edges of the Delaunay complex corresponding to the structure of FIG. 2A.
Figure 2C:
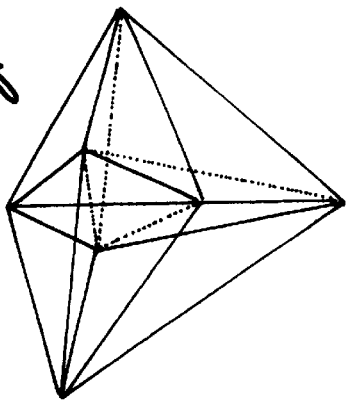
FIG. 2C is a depiction of the interior edges of the Delaunay complex corresponding to the structure of FIG. 2A.
Figure 2D:
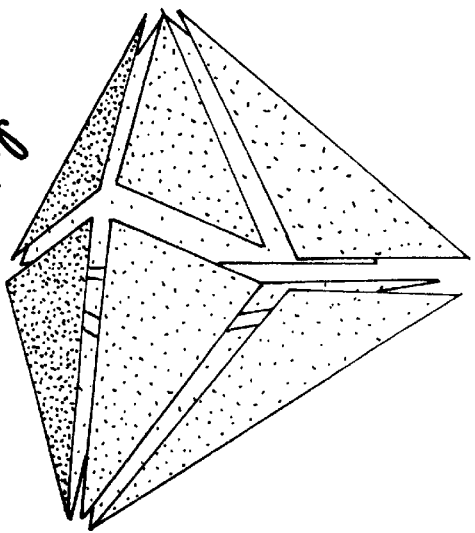
FIG. 2D is a depiction of the bounding triangles on the boundary of the Delaunay complex for the structure of FIG. 2A.
Figure 2E:
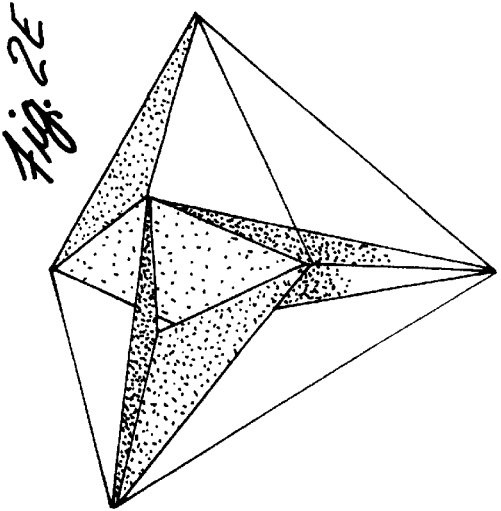
FIG. 2E is a depiction of the interior triangles of the Delaunay complex for the structure of FIG. 2A.

The present approach provides a powerful technique for classifying molecules based on geometrical constructions reflecting local structural information. The classification technique is useful for identifying and evaluating similarities and differences between molecules that may be reflected in the behavior of the molecules. For similarity searching, substructure searching and the like, an accurate and efficient description of the three-dimensional molecules provides many advantages. For combinatorial synthesis and parallel planning, it is important to sample a large compound diversity space with a well constructed representative set of compounds. The diversity space can be examined using the present classification techniques.

The basic idea for the classification is founded upon building up a framework of local structural information. The local structural information preferably includes information about an atom and its relationship with neighboring atoms. The molecular structure analysis begins with the three dimensional molecular structure given as the coordinates of the locations of the atoms in the molecule.

A space filling description of the molecule is obtained by placing possibly overlapping balls around each atomic center. Preferably, the possibly overlapping balls have diameters determined by the characteristics of the atom. The space filled description of the molecule can be decomposed using geometric constructions to represent the local structural information, preferably using a combination of topological elements of different dimensions. A collection of data representing this local structural information in a simple and compact format generally is constructed for the whole molecule to provide corresponding global structural information of the molecule. Additional property information can be included in the classification.

Initially, the structural information is used to classify the molecule according to provided criteria. The classifications provide a wealth of information for use in a variety of ways. For example, the molecular classifications can simply be used to determine the similarity and/or diversity among molecules in groups. Furthermore, the classification scheme can be used for similarity searches to identify molecular structures with a desired degree of variation from a molecule with a known structure and classification. In addition, particularly relevant features of the classification can be identified to focus the examination of relationships between molecules. These approaches can be built into systematic analyses.

The classification approaches can be applied to compounds of any type, for example, organic molecules and inorganic molecules. Similarly, the molecules can be useful for any type of application such as drugs and superconductors. Of particular interest, the approaches can be applied to relatively small organic molecules with molecular weights between about 50 daltons and about 2,500 daltons, which may be useful as drugs. Candidate compounds generally have multiple functional groups, such as amine, carbonyl, hydroxyl and carboxyl groups, that can be involved in interactions with proteins. The compounds can involve cyclic carbon moieties, heterocyclic moieties, aromatic structures or polyaromatic structures. Appropriate compounds can be biomolecules such as peptides, saccharides, fatty acids, steroids, purines, pyrimidines, derivatives thereof, structural analogues thereof or combinations thereof.

Appropriate efficacy assays can be combined with the molecular classification.

A. Molecular Classification Scheme

1. Basis Features

The classification is based on the building up of local structural information along with relationships between the local structural elements to describe the relevant properties of the molecule. Associated chemical and/or physical properties can be added to the classification.

The structural information generally is referenced relative to each atom, although the molecule can be divided according to groups of atoms such as methyl groups, methylene groups, amine groups, amino acid residues and the like, which can be treated in the analysis as if the group were an atom. The approach based on groups of atoms may be desirable for large macromolecules, and for dealing with multiple conformers. For example, both cis and trans configurations can be represented by one "atom" that has a large enough radius so that both are contained within the ball. In other words, the "atom" of large radius may contain the group in both configurations. For simplicity, the discussion below involves association of information with atoms. The analysis can be modified to include information regarding groups of atoms, if desired.

The basic features of the classification scheme are outlined in FIG. 1. The molecular structure provided as the three dimensional coordinates of the centers of the atoms provides the necessary input 102 for the molecular classification. To represent the local structure, the structure defined by the atomic centers is converted into a three dimensional body, consisting of possibly intersecting spherical balls. Thus, for the structure of interest, a radius of the spherical ball is assigned 104 for each atom. The simplest model involves the placement of a constant radius ball around each atomic center. Alternatively, a van der Waals model is obtained from the placement of a ball with a van der Waals radius around each atom. Other related molecular models such as solvent accessible and molecular surface models can be constructed from the van der Waals model to account for solvents and other interactions. In summary, the radii can be the same for all atoms, or each radius can be selected based on the particular atom identity, type of atom or property of the atom, and corresponding model for the molecule such as the solvent accessible model or the van der Waals model.

2. Voronoi Decomposition and Delaunay Triangulation

The body can be divided into Voronoi regions, where each region is associated 106 with an atom. The Voronoi region of an atom consists of the space around that atom. More specifically, the distance of every point in the Voronoi region to the atom is less than or equal to the distance to any other atom of the molecule. If the radii of the atoms are all the same then the distance to an atom can be defined as the Euclidean distance to its center. If different atoms have different radii then the distance to an atom is defined an the Euclidean distance squared to the center minus the radius squared.

Each Voronoi region reflects a wealth of information on the local structure around the atom associated with the region. The information contained in the Voronoi region can be extracted in a variety of ways. Simple ways can be used such as storing the number and identities of the neighboring Voronoi regions, which are the other Voronoi regions that a particular Voronoi region contacts along a common face. Preferably, a more systematic approach is used.

One systematic approach for associating information about the Voronoi region takes advantage of another geometric construct, the Delaunay triangulation. The Delaunay triangulation involves associating topological elements or simplices with the local relationships of atoms in the molecule. The topological elements are related to the Voronoi decomposition of the molecular body. The atomic centers define a convex body (convex hull) with a surface formed by shrink wrapping the surface tightly over the atomic centers. An unweighted triangulation can be performed by decomposing this convex body into a collection of tetrahedra with atom centers as vertices. To cleanly fill up the convex body, the surface of a tetrahedra is not allowed to cross the surface of another tetrahedra.

The Delaunay triangulation results in a collection of topological elements, collectively called a Delaunay complex. The Delaunay complex reflects the boundary overlap among the Voronoi regions described above. The Delaunay complex can be derived from the Voronoi diagram by a direct translation and contains equivalent information. If a ball has a non-empty Voronoi region, its center is a vertex in the complex. If two Voronoi regions share a common facet, the edge connecting the two ball centers is in the complex. Also, if three Voronoi regions share a common edge, the triangle spanned by the three ball centers is in the complex. Finally, if four Voronoi regions share a common point, the tetrahedron spanned by the four ball centers is in the complex. This direct correspondence applies both when all atom balls have the same radii and when the balls have different radii. It follows that the Delaunay topological elements intrinsically encode spatial nearest-neighbor information.

The Delaunay triangulation contains a wealth of information about molecular shape and structure. Performance of the Delaunay triangulation is further described, for example, in V. T. Rajan, "Optimality of the Delaunay triangulation in $R^d$," Discr. Comput. Geometry, 12:189–202 (1994), and a detailed implementation procedure is described in M. A. Facello, "Implementation of a randomized algorithm for Delaunay and regular triangularizations in three dimensions," Computer Aided Geometric Design, 12: 349–370 (1995), which is based on H. Edelsbrunner and N. R. Shah, Algorithmica, 15: 223–241 (1996), all three of these publications incorporated herein by reference. When the radii of the atoms are unequal the triangulation is referred to as a weighted Delaunay triangulation.

3. Weighted Delaunay Triangulation

Preferably, a weighted Delaunay triangulation is performed. In a weighted Delaunay triangulation, an atom is represented by the coordinates of its center in three dimensional space and the weight of an atom q, $$w_q = r_q^2,$$

where $r_q$ is the radius of the atom. The power distance $\pi$ between a point p and an atom center q is defined as $$\pi_p(q) = |pq|^2 - w_q,$$

where $|pq|$ is the Euclidean distance between p and q. For a tetrahedron abcd, there is a unique point z, the orthogonal center, that has the same power distance $w_z$ to the four atom centers at points a, b, c, and d. The unique power distance $w_x$ can be thought as the weight of the orthogonal center.

For a triangle abc with atom centers at three dimensional points a, b and c, two tetrahedra abcd and abce may share the interfacial triangle abc. If the power distance of e to z, the unique orthogonal center for tetrahedron abcd, is larger than the weight of e (i.e., $$\pi_z(e) > w_e),$$

this triangle abc is called "locally regular." Similarly, if the triangle is incident to only one tetrahedron, it is locally regular.

The weighted Delaunay triangulation can be performed based on these values. Given a set S of atoms and associated atomic center coordinates and atomic radii, the triangulation is performed by taking a helper tetrahedron large enough so that all atoms are contained within it. Formally, the vertices of the helper tetrahedron can be placed at infinity initially. None of the vertices correspond to an atomic center at this point. The initial triangulation consist of this single helper tetrahedron.

Then, an arbitrary atom $p_i$ from the molecule is added to the current existing triangulation. The particular tetrahedron abcd that contains point $p_i$ is then identified. If the power distance of $p_i$ to the unique orthogonal center of the identified tetrahedron is less than the weight of $p_i$, i.e., $r_{pi}^2$, $p_i$ is included for updating the triangulation. To update the triangulation, the identified tetrahedron is replaced with four new tetrahedra, each with $p_i$ as a vertex. Initially, the identified tetrahedron is the helper tetrahedron, which is replaced by four new tetrahedra each having $p_i$ as a vertex. As long as a tetrahedron has a vertex from the helper tetrahedron, the tetrahedron has an orthogonal center at infinity and is replaced in a later step of the triangulation.

Next, each of the four triangular facets of the new tetrahedra that are directly across from vertex $p_i$ are checked to determine if they are locally regular. If a triangular facet is not locally regular, a flip operation is performed to remove the offending triangle by replacing the involved tetrahedra with a different set of tetrahedra, which occupy the same space. In the simplest case there are two involved tetrahedra that form a convex triangular double pyramid. The flip operation replaces the two tetrahedra by three new tetrahedra arranged in a cycle around the new edge that connects the top apex with the bottom apex of the pyramid. It is also possible that the two involved tetrahedra form a non-convex double pyramid. In this case the flip cannot be performed as described.

Instead, a determination is made whether there is a third tetrahedron that fits with the two to form a convex double pyramid. If this is the case, the flip replaces the three tetrahedra by two new tetrahedra sharing the new triangle that decomposes the double pyramid into two single pyramids. If there is no fitting third tetrahedron, it is still possible that there are two additional tetrahedra that fit with the first two tetrahedra to form a larger tetrahedron. In this case, the flip replaces the four tetrahedra by the new larger one.

Finally, if such additional one or two tetrahedra do not exist, no flip operation can be executed, and the offending triangles remain in the triangulation temporarily. It can be shown that if there are any non-locally regular triangles, there is at least one offending triangle that can be removed by a flip operation, see the reference by Edelsbrunner and Shah, above, incorporated herein by reference. The flips that can be performed change the neighborhood of other offending triangles until each can be removed by one of the three types of flips described above. The process stops when no offending triangles remains.

4. Descriptors for Topological Elements

Upon completion of the triangulation, the group of tetrahedra can share common vertices, edges or triangles. More formally, any two tetrahedra are either disjoint, or they intersect at a common triangle, edge or vertex. The triangulation is represented by a simplicial complex, i.e., a collection of simplices. The dimension of the simplices are as follows: 0-simplices for vertices, 1-simplices for edges, 2-simplices for triangles and 3-simplices for tetrahedra.

The Delaunay triangulation guarantees that if an edge belongs to the complex, its endpoints are vertices in the complex. Similarly, if a triangle belongs to the complex, the edges of the triangle are in the complex, and if a tetrahedron belongs to a complex, the triangles of the tetrahedron also belong to the complex. This enumeration accounts for all intersection patterns. The vertices, edges, triangles and tetrahedra form the set of topological elements associated with the molecule. These topological elements are collectively indicative of the overall geometrical structure of the molecule. An advantage of using a weighted Delaunay triangulation is the construction of a precise description of the shape of a molecule corresponding to atoms within the molecule with different radii.

The information corresponding to the topological elements, i.e., vertices, edges, triangles and tetrahedra preferably is stored for further processing. The topological elements provide a vast amount of information in a compact format. The Delaunay triangulation of any n points in 3D has at most $(n^2-n)/2$ edges, $n^2-3n$ triangles and $(n^2-3n-2)/2$ tetrahedra. In molecules, the number of topological elements tends to be significantly less than the above maximum values because atoms usually pack in the occupied space, and they cannot be too close to each other due to bond length restrictions. The total number of topological elements is empirically on the order of n, in other words a small constant multiplied by n, n being the number of atoms. The construction of the Delaunay complex takes a quantity of time that is typically a factor of logn multiplied by the number of simplices, i.e. on the order of nlogn. Therefore, Delaunay triangulation is a fast and efficient method for generating 3D shape descriptors.

An identification (ID) of a topological element of dimension m-1 can be defined as an m-tuple of integers in sorted order. An integer (e.g., i) in the m-tuple indicates that the corresponding atom is the i-th atom appearing in the input structure file. This ID of sorted integers provides a unique canonical label for each topological element. For example, a tetrahedron abcd can also be written as acdb, bacd, dcba, etc., but all of these have the same canonical label identifying them as the same tetrahedron.

The construction of the topological elements generally is a starting point for a systematic analysis of structure of a molecule. This information alone could be used to perform molecular classification, as described below. Preferably, additional local-structural and/or property information is assigned 108 to complete the structural information assembly for processing in any later classification.

5. Characteristic Alpha Values

Additional information can take the form of size (or characteristic alpha value) of the topological elements. Size information can be obtained in a systematic way using another geometric construct, the alpha complex. When atoms have the same radii, the unweighted alpha complex can be obtained by growing a ball around each atomic center simultaneously at the same rate. A ball only grows inside its own Voronoi region and is clipped when it reaches the boundary of this region. An alpha value is collected when the clipped balls growing from all the vertices of a topological element have a common boundary intersection.

The topological elements from the Delaunay complex are ordered based on the a value when each appears. At the beginning when the radius is small, there are only vertices and the atomic centers are the first topological elements of the sequence. When the boundaries of two balls overlap, the corresponding edge in the Delaunay complex is added to the end of the corresponding sequence of elements. When the boundaries of three balls overlap, the corresponding triangle in the Delaunay complex is added to the sequence. Similarly, when the boundaries of four balls overlap, the corresponding tetrahedron is added to the sequence. When two balls grow, bounding spheres intersect in a circle that lies on the plane bisecting the line segment connecting the atomic centers. A portion of the plane makes up a facet in the Voronoi diagram.

Thus, all of the topological elements are organized into a sequence. In topology, the sequence of elements is called the filter of the Delaunay complex. If a number of simplices from the beginning of the sequence is selected sequentially and no simplex is skipped along the way, this sequence is a collection of simplices that itself forms a complex. It is a subcomplex of the Delaunay complex. The sequence of such subcomplexes is called a filtration of the Delaunay complex. This organization of subcomplexes within the filter is an important property of the filter.

This process for ordering the simplices, i.e., topological elements, can be generalized for the case of unequal sized balls. To do this, a van der Waals radius, $R_d$, can be associated with each atom. The radii of the balls can be changed by altering a parameter alpha ($\alpha$), where the altered radius is given by $$r_\alpha = \sqrt{r_o^2 + \alpha}$$

$\alpha^2$ can be any real number, also negative. In case the value under the root is negative, $r_\alpha$ is imaginary, and the ball is considered to be empty or non-existent for this value of alpha. The sizes of the balls as determined by alpha are varied according the procedure outlined above for equal sized balls. Again, a sequence of Delaunay simplices is obtained that can be used as a filter.

Using this model, any vertex element is assigned a characteristic value ac such that $\alpha_c = -r_0^2$. For an edge element, $\alpha_c$ takes the value when the two corresponding inflated/shrunken atoms meet at one point in space. For a triangle element, $\alpha_c$ takes the value when three inflated/shrunken atoms meet at one point in space. For a tetrahedron, $\alpha_c$ takes the value when the four inflated/shrunken atoms meet at one point. The $\alpha_c$ value assigned to a tetrahedron is actually the weight of the orthogonal center of the tetrahedron. After computing the $\alpha_c$ values for all topological elements, the elements can be ordered into a list by the increasing or decreasing order of $\alpha_c$. Additional discussion on the evaluation of the alpha values is found in H. Edelsbrunner and E. P. Mücke, "Three-dimensional alpha shapes," ACM Transactions Graphics, 13:43–72 (1994), incorporated herein by reference.

6. Alpha Complex

Every topological element has a characteristic $\alpha_c$ value, as defined above. An alternative view of the described process considers alpha as an adjustable parameter that defines a size scale around each atomic center based on a radius determined by alpha. The continuous family of alpha values defines a discrete family of shapes ranging from the empty set (when $\alpha$ is very small) to the convex hull of the set of atom centers (when a is very large). Alpha can assume any real value. By controlling the real parameter $\alpha$, a series of shapes can be obtained reflecting the molecule at different resolutions. Each series of shapes involves no approximations.

At any particular alpha value, the basic elements or simplices in the alpha complex can be classified as one of three types: 1) an interior element, 2) a bounding element or 3) a singular element. Bounding elements are on the surface or boundary of the alpha complex and form the face or edge of another simplex of higher dimension. A singular element is on the surface or boundary of the alpha complex but is not a face or edge of any simplices of higher dimension.

To classify the simplices at a particular value of alpha, a simplex $\sigma$ has an associated value $\mu$, which is the smallest characteristic alpha value of all of the simplices of one higher dimension that contains $\sigma$ as a face, and simplex $\sigma$ has an associated value $\tau$ that is the largest characteristic alpha value of all these simplices. Observe that the characteristic alpha value of $\sigma$ is either smaller than or equal to $\mu$, but it cannot be larger than $\mu$.

Consider an arbitrary but fixed value of alpha that defines a fixed alpha complex. A simplex $\sigma$ belongs to that complex exactly if the characteristic alpha value for $\sigma$ is less than that fixed alpha value. The type of sigma can be decided by comparing alpha with the values of $\mu$ and $\tau$ associated with $\sigma$. If $\sigma$ is a simplex on the convex hull and if alpha is smaller than its associated value $\mu$, the simplex is singular. If alpha is larger than $\mu$, the simplex is bounding. For $\sigma$ being a simplex in the interior of the Delaunay complex, $\sigma$ is singular if alpha is smaller than $\mu$, $\sigma$ is bounding if alpha is between $\mu$ and $\tau$, and $\sigma$ is interior if alpha exceeds $\tau$. Since tetrahedra are not a face of any elements of the triangulation, a tetrahedron is automatically interior, provided the tetrahedron belongs to the alpha complex. For further details, see Edelsbrunner and Mücke, above, incorporated herein by reference. This method applies for any alpha value, but the case of $\alpha=0$ is of most interest since this corresponds to the van der Waals model of the molecule.

To exemplify the triangulation of a particular molecule, FIG. 2 depicts a weighted Delaunay triangulation for the heavy atom backbone of a valine amino acid fragment. The molecular structure is shown in FIG. 2A. The bounding edges of the Delaunay complex are depicted in FIG. 2B while the interior edges are noted with darkened lines in FIG. 2C. FIGS. 2D and 2E show the bounding triangles on the boundary of the Delaunay complex and the interior triangles, respectively. The tetrahedra are shown in FIG. 2F.

For a particular value of alpha, the associated alpha complex is a subcomplex of the Delaunay complex. A characteristic of the filter property is that the alpha complex for a smaller value of alpha is included in the alpha complex for a larger value of alpha. In other words, an alpha complex for one value of alpha is necessarily a subcomplex of the alpha complex for a larger value of alpha.

The alpha complex provides a systematic way of storing additional information related to the local structure. The correspondence between the molecule and its alpha complex provides the ability to obtain general area and volume information without constructing a geometric model of the molecule. See, H. Edelsbrunner, "The union of balls and its dual shape," Discrete and Computational Geometry, 13:415–440 (1995), incorporated herein by reference; and H. Edelsbrunner, M. Facello, P. Fu and J. Liang, "Measuring Proteins and Voids in Proteins," Proc. 28th Ann. Hawaii Int'l Conf. on System Sciences, IEEE Computer Society Press, 256–264, incorporated herein by reference. For example, when $\alpha=0$, the alpha complex reflects the topological structure of the molecule and can be used to identify voids and pockets in proteins and other macromolecules.

7. Star and Link Relations

In addition, information relating to relationships between topological elements produced by the triangulation can be associated with elements of the Delaunay complex. For example, the star relationship for each element can be computed and accessed. For a vertex, the 1-0 star involves all edges with the vertex as one endpoint, the 2-0 star involves all triangles with the vertex as a corner and the 3-0 star involves all tetrahedra with the vertex as an apex. Similarly, for an edge the 2-1 star involves all triangles with the edge as a side, and the 3-1 star involves all tetrahedra with the edge as a side. Finally, for all triangles the 3-2 star involves all tetrahedra with the triangle as a face.

The star relationships provide second nearest-neighbor information. The star relationship is inherent in the representation of the Delaunay complex and can be evaluated as needed. Based on the data structure of the Delaunay complex, the star can be evaluated with minimal computational effort. In this data structure, each tetrahedron $\sigma$ is stored in its own block of memory. This block includes the addresses of up to four adjacent tetrahedra, which each share a triangle with $\sigma$, and the addresses of the four vertices, which are line numbers of the four input atoms. From this information we can find the faces of $\sigma$ as well as the faces of adjacent tetrahedra in constant time. The simplices in the star of another simplex are enumerated by collecting faces of adjacent tetrahedra, each in constant time.

A star relationship can also be defined for an alpha complex. For example, instead of a collection of all triangles that share a vertex "a", the 2-0 star of "a" for a particular alpha complex is a subset of the previous collection of triangles, each satisfies the condition that their characteristic alpha ($\alpha_c$) values are no larger than the value of alpha defining the complex. Such alpha-star relationship provides neighbor information for a vertex up to the specified resolution, $\alpha$.

In addition to the star relationship between topological elements, there is the link relationship. For a topological element $\sigma$, the link is the collection of elements that do not touch a but "link" $\sigma$ to the rest of the Delaunay triangulation. More specifically, elements in the 1-0 link for a vertex v include an edge xy if xyv is a triangle in the Delaunay complex. The collection of all such edges is the 1-0 link of the v vertex. Similarly, elements in the 2-0 link for a vertex v include a triangle xyz if xyzv is a tetrahedron in the Delaunay complex. The collection of all such triangles is the 2-0 link of the v vertex. The 0-1 link for the ab edge is the collection of vertices c such that abc is a triangle in the Delaunay complex. Also, the 1-1 link for an edge ab is the collection of edges cd such that the tetrahedron abcd is in the Delaunay complex. The 0-2 link of a triangle abc is the collection of vertices d such that the tetrahedron abcd is in the Delaunay complex. In addition, the 0-0 link of a vertex a is the collection of vertices b such that the edge ab is in the Delaunay complex. Links can also be defined for the alpha complex in the same way as described for stars, i.e., the subset of a link with $\alpha_c$ values no larger than the specified a is the corresponding $\alpha$ link.

Links can be constructed by going through all relevant types of elements in the weighted Delaunay triangulation. For example, to construct the 2-0 link for a vertex v, we check all Delaunay tetrahedra for those containing v, the triangles given by the rest of the three vertices form the 2-0 links of v. Considerable computational savings can be achieved if stars are constructed first. For example, instead of checking all Delaunay tetrahedra to obtain the 2-0 links of v, only the tetrahedra in the 3-0 star of vertex v have to be checked.

8. Additional Properties

The process can be continued by associating additional properties related to the local structure with the topological elements. For example, the type of atom can be associated with a vertex. A variety of other atomic properties can be associated with vertices, for example, location at the surface of the molecule, location in an interior cavity, location on the convex hull, polarity of the atom, electron donor characteristic, electron acceptor characteristic, electrophilicity, nucleophilicity and hydrogen bonding behavior. Properties that are either present or absent can be represented by a one bit digit in a program implementing the process. Other parameters can be stored as appropriate.

For an edge, possible properties include the existence or absence of a bond between the atoms, the polarity of the bond and the like. Similarly, for a tetrahedron the orientation can be stored. The orientation of a tetrahedron can be defined according to a variety of possible schemes. In a preferred scheme, the orientation is evaluated using the sequence of atoms in the canonical label of the tetrahedron. Specifically, the orientation of a tetrahedron with canonical label of abcd is evaluated to be +1 or −1 from the sign obtained by calculating the determinant:

$$\begin{vmatrix} a_1 & a_2 & a_3 & 1 \\ b_1 & b_2 & b_3 & 1 \\ c_1 & c_2 & c_3 & 1 \\ d_1 & d_2 & d_3 & 1 \end{vmatrix}$$

where $a_1$, $a_2$, $a_3$ denote the x, y and z coordinate of atom center a and similarly for atoms b, c and d, the atoms being orderer in the determinant based on the canonical ordering. The sign of the orientation indicates on which side of the plane through b, c and d the point a lies. The determined orientation thus can be used for denoting the chirality of atoms.

For applications, the orientation can be reexpressed in terms of a non-canonical label. To construct the non-canonical label, the four atoms are first ordered based on the increasing/decreasing values of the element numbers in the periodic table. If two or more atoms have the same element number, they can be ordered based on the number of covalent bonds to the atom. Atoms can be further distinguished in the label by rules such as ordering based on the sum of element numbers of all bonding partners of an atom. Upon completion, all of the atoms are ordered within the non-canonical label.

For each topological element, the information associated with its lower-dimensional face can also be associated with the element itself. For example, each of the properties of the two vertexes of an edge can be associated with that edge.

9. Classification Schemes

Several approaches have been described for storing local structural information and relationships between the local regions as an efficient way to organize structural information on the molecule. An important step then is to classify the molecular structures based on the structural information. The results of the classification can then be applied, as described below.

The classification can be performed in a variety of ways. Generally, a classification scheme is determined by selecting important structural and property features and associating these features with particular topological elements, relationships and properties that are described in the previous sections. For example, structural analysis of an enzyme binding site may reveal certain structural patterns for a suitable pharmacophore, providing both geometric and chemical information such as distances between functional groups and hydrophobicity characteristics. Alternatively, geometric and chemical information can be extracted from known pharmacological compounds. This information can be associated, for example, with Delaunay simplices within certain range of $\alpha_c$ values and of certain chemical properties. These simplices then can be included as part of the classification parameters useful for searching for active compounds for this target enzyme. In general, selection can be made, for example, from the Delaunay complex, the alpha complex, the star relations and the link relations. The selected items then can be defined to be the classification parameters for a structural relation assembly and are input 110 into a classification scheme for further processing.

Specifically, the classification could involve simply identifying whether a particular atomic grouping is present or not, such as the presence of a tetrahedron with vertices that are a nitrogen atom, a carbon atom, and oxygen atom and a hydrogen atom. Of course, much more complex classification schemes can be presented. The classification parameters are used to classify 112 the molecule using the structural relation assembly constructed for the molecule.

The selection of a particular classification approach depends on the nature of the local information available. If information is stored regarding the location of an atom on the convex hull, the classification can be based on an atom involved in a particular local structure being on the convex hull of the molecule.

The classification procedure can be made more systematic, if desired. FIG. 3 outlines a preferred approach to systematically constructing a structural information assembly for a molecule. The 3D molecular structure is input 120 in the form of the coordinates of the atomic centers. The 3D molecular structure inherently includes conformational information along with the identification of the type of atoms. Atomic radii are assigned 122 for each of the atomic centers. Based on the atomic radii, a Delaunay triangulation is performed 124 to compute the associated topological elements.

Next, optional structural elements are evaluated. If desired, characteristic alpha values ($\alpha_c$) are evaluated 126 for elements. Star and/or link relations can be computed 128, if desired. Similarly, other structural or property information optionally is assigned 130 with the topological elements. All of the structural and property information preferably is assembled and placed 132 into a file or database record. For example, a record could include the following fields: one for the molecular identifier such as an ACS number, one for a conformational identifier and the remaining fields for 3D shape descriptors and for associated properties.

Each descriptor field can be constructed with two subfields: one for the total number of occurrences of the descriptor and a second for the address in memory or storage of the block of values for the descriptor. The block of values can in turn contain a first part with 3D shape descriptors and a second part with property descriptors associated with the topological elements.

Figure 2F:
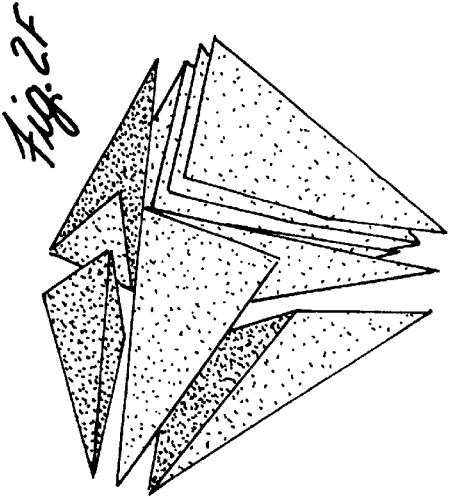
FIG. 2F is a depiction of the tetrahedra of the Delaunay complex for the structure of FIG. 2A.

The 3D shape descriptors to be recorded at the blocks of values can include all of the topological elements from the triangulation or only a portion. For example, all tetrahedra and bounding triangles together with associated $\alpha_c$ values, or all tetrahedra and all triangles on the boundary of the alpha complex for $\alpha=0$ alternatively can be selected. A preferred selection would include all tetrahedra, singular and bounding triangles and singular edges (independent edges) based on a balance of information content and storage economy A relatively simple example, the Delaunay simplices of a valine amino acid fragment are computed, as shown in FIG. 2. The $\alpha_c$ values can be evaluated for the boundary edges (FIG. 2*b*), the interior edges (FIG. 2*c*), the boundary triangles (FIG. 2*d*), the interior triangles (FIG. 2*e*), and the tetrahedra (FIG. 2*f*). Additional property information such as H-bond mark of 1 donor/acceptor can be assigned to the boundary edges and interior edges as well as boundary triangles and interior triangles involving the O atom (bottom atom in dark) and the N atom (rightmost atom in dark gray). The elements with their $\alpha_c$ and H-bond information are then placed into a record. A field in the record for the descriptors of the boundary edge type includes: 1) the total number of such edges in the fragment, and 2) an address to the block values of the descriptors. The first part of the block values for the boundary edges have the $\alpha_c$ values. The second part of the block values have the chemical information, in this case an H-donor/acceptor indicator.

To complete this preferred classification scheme, classification parameters are input 134. The user inputs the shape and physicochemical parameters that are significant and to be examined. Preferably, a tolerance range is input for each of the classification parameters to form the basis for comparison. Elements can be found similar even if not identical.

For example, the user could decide that any topological tetrahedra are similar if they have a characteristic a value of about 5 Å and differ by less than 0.5 Å. Additional restrictions can be placed such as requiring that the four atoms have the same number of H-donor/acceptors and the same number of hydrophobic atoms. The orientation of the four atoms can be included. Similar criteria can be devised for other topological elements (triangles, edges and vertices).

For relations like star and link, criteria can also be specified. For example, two 3-0 stars to an oxygen atom could be considered to be similar if each contains the same number of tetrahedra, and the characteristic a values of the tetrahedra fall into the same range. The methods described are flexible for the selection of criteria to be input by the user for the selection of a desired classification scheme. The criteria can be based on topological elements, associated relationships and other properties relating to the topological elements. The assembly of structural information is evaluated 136 based on the classification parameters.

A preferred embodiment for the characterization procedure for a group of molecules, entitled Topological Data Assembler, is summarized in FIG. 4. The three dimensional structures of a group of molecules are input 152 to provide necessary information for the procedure. For each of the molecules, the 3D shape elements and relations and property descriptors are evaluated and stored in a file/database record 154. Next, the frequency of elements and relations is analyzed 156. This can be done, for example, by constructing a histogram according to the $\alpha_c$ value of an element or relation deemed important. The range of $\alpha$ values covering most interesting features can be determined from the histogram.

Then, bins can be defined such that each bin is associated with a value range for a particular descriptor. A particular item for the descriptor goes into a particular bin based on the ranges associated with the bins and the value of the descriptor for this item. The number of bins N to be stored for each element is input 158. Also, the classification parameters are input 160. Based on N, the frequency histograms can be analyzed to determine the range of values, e.g., $\alpha_c$, for elements to be placed in the N bins. The range of $\alpha_c$ is then divided according to the number of bins. The percent of values grouped into each bin is given by $1/N \times 100\%$. If a 32 bit string is used, N=32 and 100/32% are grouped into each bin. In this way, the range of values for each bin is determined 162, i.e., each value of the parameter is assigned a bin number 1–32 for a 32 bit string. Other schemes of user defined ranges for each bin can also be used.

Then, for each molecule 164 the bin values are determined 166 based on the value of the parameter for that molecule. The values for all bins can be initialized as 0's. When binary values are desired in the interest of economy, a "1" value is placed in the corresponding bin when the represented shape or property feature for the bin is present in the molecule. When real values are desired, the number of elements falling into each bin can be assigned as the bin value. If N bins are used for each feature, and if L features are chosen as important, L number of N-bin arrays correspond to the descriptors for each molecule. After processing M molecules, the data can be assembled 168 into a M×N×L matrix.

B. Applications of the Classification Scheme

1. Similarity Comparisons

An important use of the classification scheme is in the evaluation of the similarity or differences between two or more molecules. One approach is to apply a scoring scheme whereby the score reflects the similarity between the molecules. The score is evaluated using the structural descriptors defined for the molecules.

As a simple example, assume that compound i has $|T_i|$ number of topological elements of selected categories and that compound j has $|T_j|$ such topological elements. The symbol "$|A|$" denotes the number of elements in a set A. $T_k$ are the descriptors, such as topological elements, relations and associated properties in selected categories, for compound k. When descriptors are topological elements, we use the chemically-sorted (non-canonical) label derived from the chemical elements and bond valences of the atoms, rather than the canonical labels based on the line numbers in the input file since the canonical labels are less amenable for comparison between different molecules. Then, $|T_i \cap T_j|$ denotes the number of topological elements or other descriptors common to both compounds. The similarity measure between the two compounds, for example, can be computed as:

$$S(i, j) = \frac{2|T_i \cap T_j|}{|T_i| + |T_j|}$$

A variety of variations on this definition of the similarity measure can be used, as desired.

Furthermore, this procedure can be generalized. For example, different weights can be given to different topological elements and property descriptors for a molecule. The descriptors are denoted $\sigma_k$ where $k=1,N_i$, and $N_i$ is the total number of descriptors for molecule i. The weight for a given feature is $w_k$. For a second molecule j, the corresponding values are $\sigma_l$, $w_l$, where $l=1,N_j$. It is required that the weights of matching features are the same, i.e., $w_k=w_l$ if $\sigma_k=\sigma_l$. The similarity measure between molecules i and j is $$S(i, j) = \frac{2 \sum w_n \cdot \sigma_n}{\sum w_k \cdot \sigma_k + \sum w_l \cdot \sigma_l}$$

where $\sigma_n$ denotes a feature common to both molecules and $w_n$ is the corresponding weight.

Figure 5:
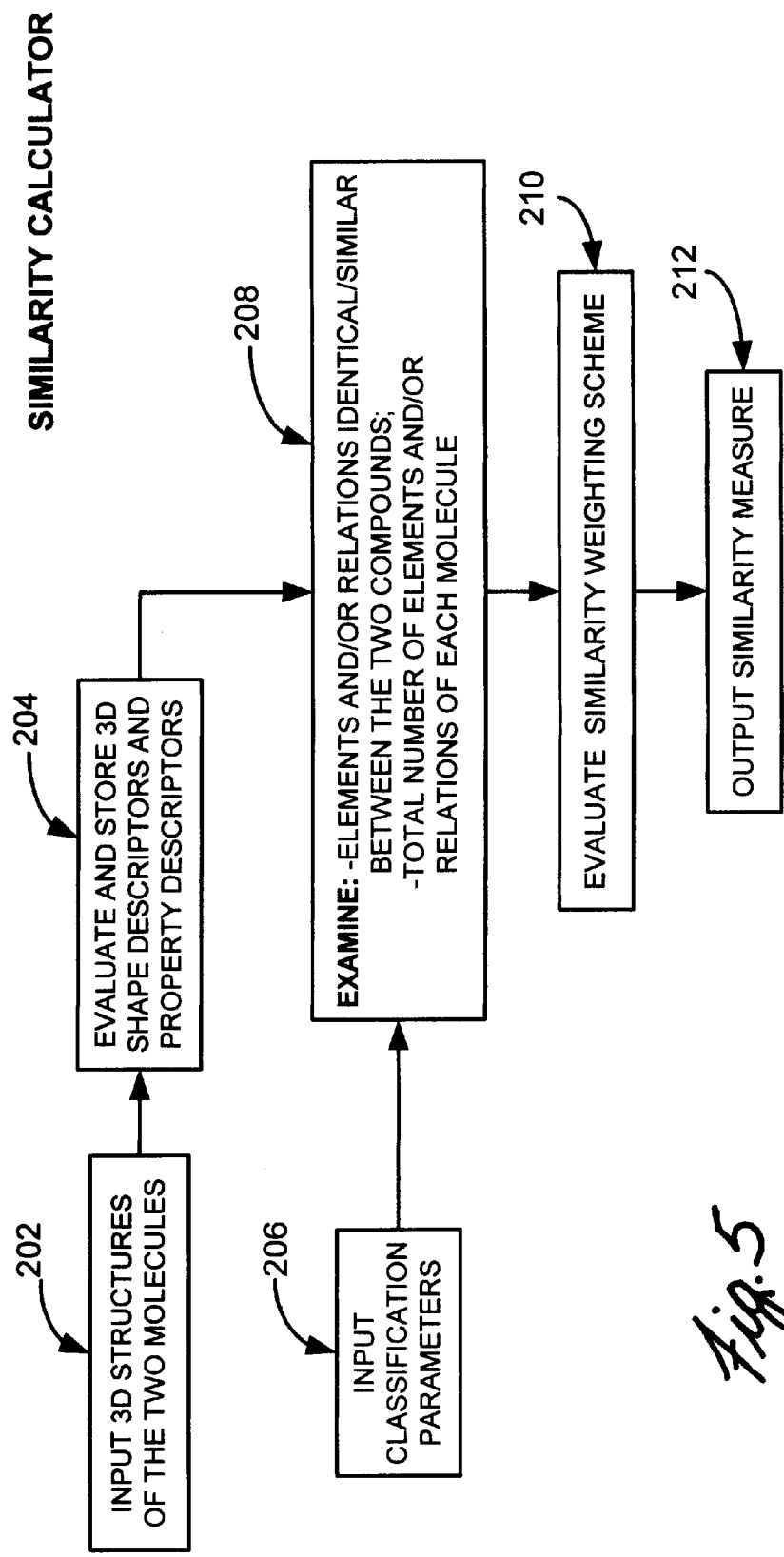
FIG. 5 is a flow chart outlining the evaluation of the similarity/differences between two molecules.

The similarity measures can be implemented in a systematic way. Referring to FIG. 5, the 3D structure of the two molecules is input 202 as the coordinates of the atomic centers. The shape descriptors and the property descriptors are evaluated 204. A classification scheme is determined and input 206 in the form of classification parameters. The shape descriptors and property descriptors that are included in the classification parameters are examined 208 to determine if they are identical or similar between the two molecules. Next, the similarity measure is evaluated 210 based on one of the above similarity measures of a comparable measure. The similarity measure is output 212.

2. Database Similarity Search

Figure 6:
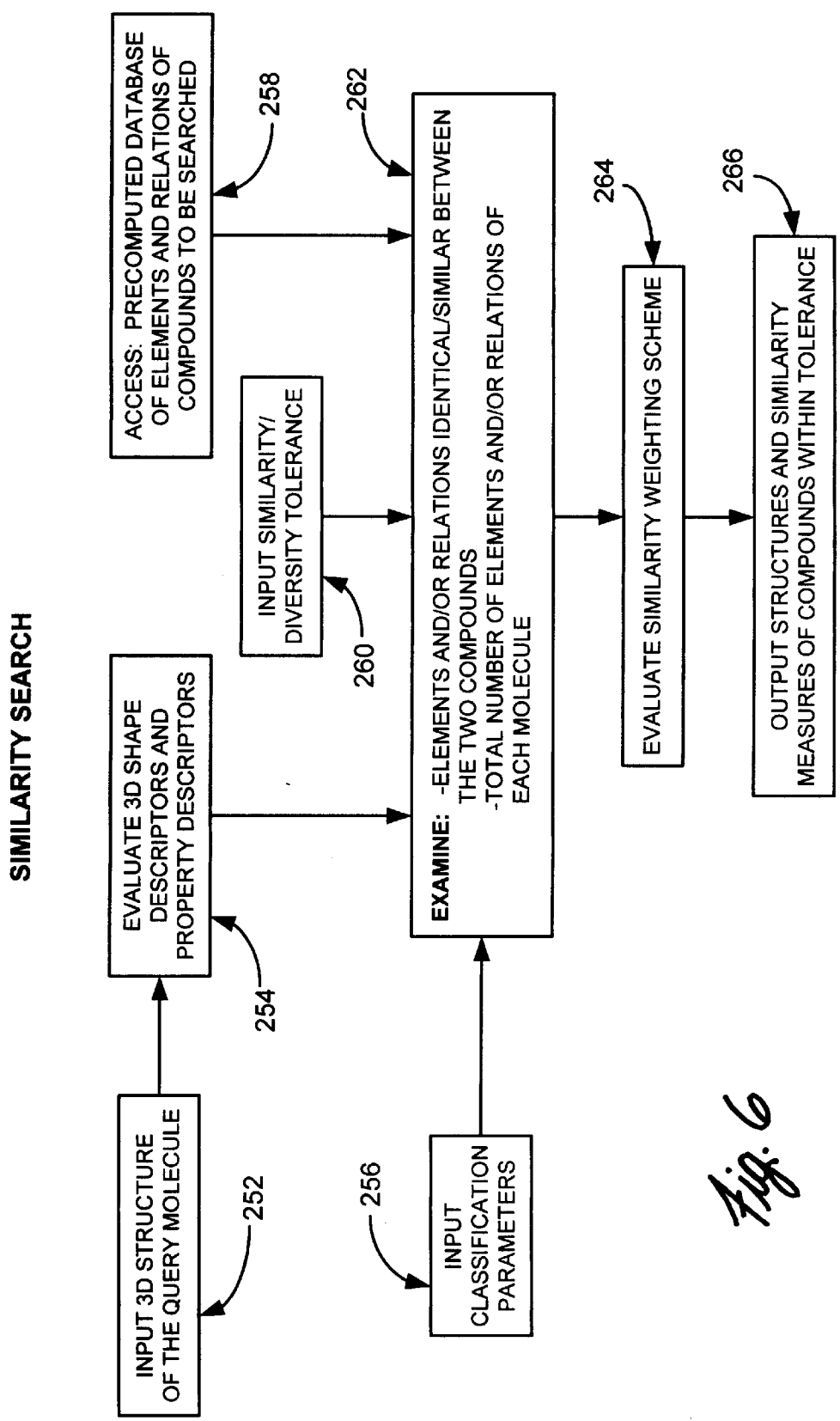
FIG. 6 is a flow chart outlining a similarity search for molecules in a database based on the classification of a query molecule.

The above process can be adapted for a database search. Referring to FIG. 6, the 3D structure of a query molecule is input 252. The shape descriptors and property descriptors are evaluated 254, as described above. A classification scheme is determined and input 256 in the form of classification parameters. In order to perform comparisons, a precomputed database containing elements and relations, i.e., shape descriptors and property descriptors, are accessed 258. The database contains information on a set of compounds. These compounds can be compounds, for example, that are available for screening.

Preferably, tolerance ranges are input 260 for each of the classification parameters. Using the shape descriptors and property descriptors for the query molecule and the values in the database, the elements and relations are examined 262 to determine if they are identical or similar between the query molecule and the molecules in the database. The comparisons are used to evaluate 264 a similarity measure. The structures and similarity measures are output 266 for molecules in the database sufficiently similar to the query molecule as specified by the tolerance parameters. The molecules output are generally candidates for further assaying for activity comparable to the query molecule.

The desire is to identify molecules with potentially similar or improved activities relative to the query molecule. The results of the similarity search can be used to perform activity assays, possibly using the principles of combinatorial chemistry. In other words, a combinatorial chemistry library can be constructed based on the database search results. Similarly, the results of additional activity assays can be used to refine the structural and property classifications and/or to suggest additional query molecules for database searching and lab screening. Such schemes are particularly helpful for drug discovery.

3. Database Construction and Clustered Databases

The scope of the database can be varied as desired. In principle, the database could be continuously expanded to account for an ever increasing range of compounds. Alternatively, the database could be constructed to include only compounds in a similar class. A simple database would involve the storage of all the shape descriptors and the property descriptors for the range of molecules covered by the database. Similarly, a comprehensive database can be organized into a clustered database.

Figure 7:
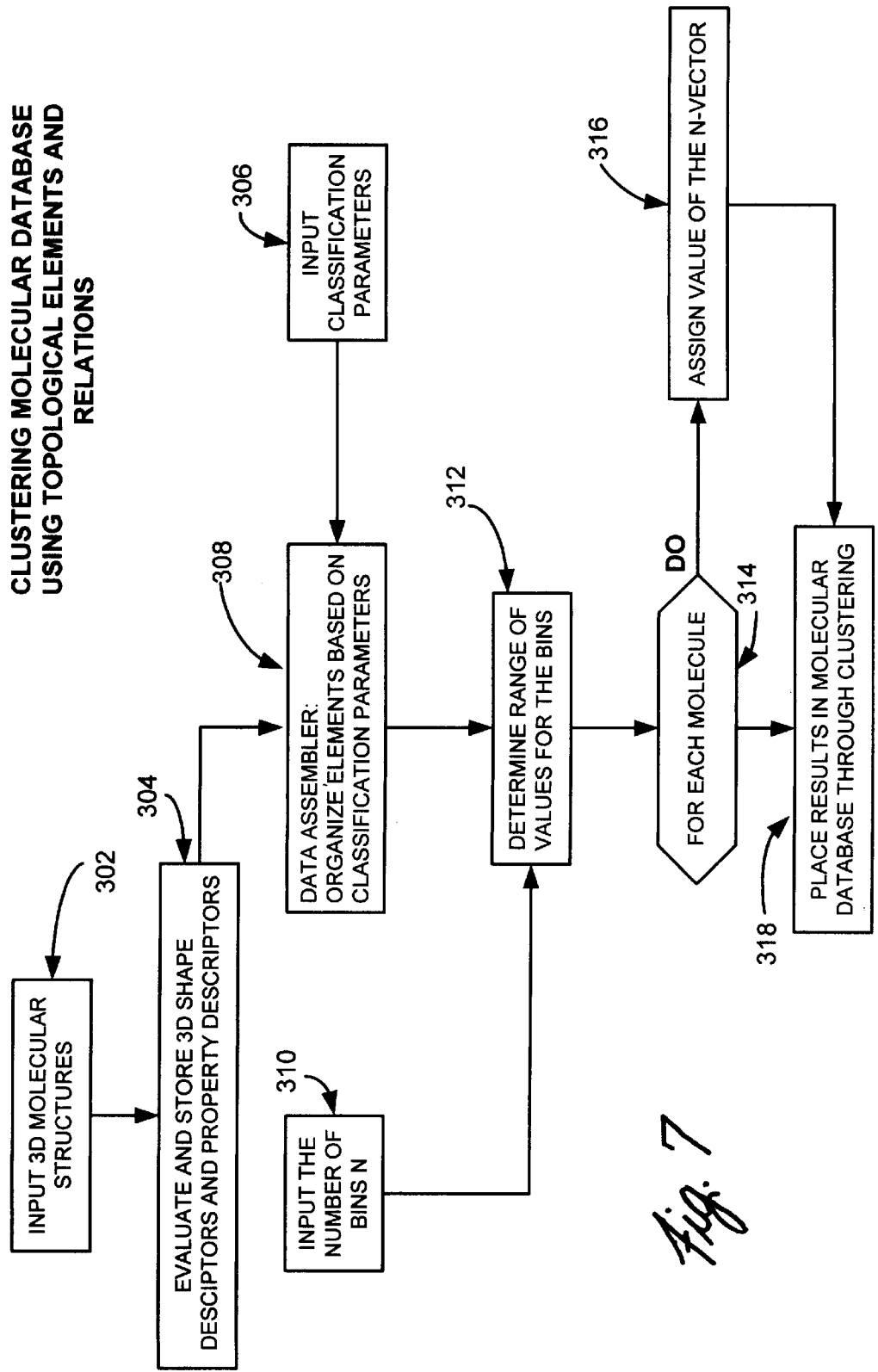
FIG. 7 is a flow chart outlining the construction of a clustering molecular database.

A procedure for constructing a clustered molecular database is outlined in FIG. 7. The 3D structures of the molecules are input 302 in the form of coordinates of the atomic centers. Based on assigned atomic radii, the shape descriptors and property descriptors are evaluated 304 for the molecules. The classification parameters are input 306 as the basis for further evaluation. The classification parameters are used to organize 308 the evaluated shape and property descriptors. Unnecessary shape and property descriptors can be discarded, the dimension of parameters correspondingly reduced (e.g., by principle component analysis) and the remaining elements, for example, organized into a matrix for the z number of relevant elements, relations and properties, and the m number of molecules.

The number of bins N for each relevant parameter is input 310. The range of values for each bin is determined 312, i.e., any value of the parameter corresponds to a bin number such as 1–1024 for a 1024 bit string, as an example. Then, for each molecule 314 an N-bit value is assigned 316 to the binary N-vector, each bit corresponding to the presence/absence of the parameter in a particular range of values. The results are further clustered and placed 318 in the clustered molecular database. The clustered molecular database is organized according to clusters of the data, in this case the bins form clusters. The clustering depends on the classification parameters and the scale of the data.

Referring to FIG. 8, the clustered molecular database can then be used for similarity searches. The 3D structure of a query molecule is input 352. The structure of the query molecule is used to evaluate 354 shape descriptors and property descriptors for the query molecule. The clustered molecular database is accessed 356, and the cluster closest to the query molecule is determined 358 based on evaluation for the query molecule of the classification parameters used to construct the clustered database.

The similarity measures between the query molecule and molecules in the cluster are evaluated 360 following the procedure outlined in FIG. 5. The desired tolerances for the similarity comparison are input 362. The molecules of the database cluster are ranked 364 according to their similarity values. The structures of the ranked molecules within the tolerances are output 366 with their similarity measures. Note that the similarity measures can involve a combination of similarity measures associated with different parameters.

4. Application of Similarity Measurements

Several specific uses for similarity comparisons already have been presented. There are additional uses directed to infrastructure management that are the topic of this section.

Diversity planning for combinatorial library construction plays an increasingly important role. Even with state-of-the-art high throughput assays, the number of compounds that can be sampled are necessarily limited relative to the huge number of possible compounds. An efficient approach to focusing in on the best candidates involves an initial screen involving a small number of compounds that are representative of the full diversity space appropriate. The topological element and relation based classification method herein provides a powerful method for rigorously analyzing and planning such a representative set of compounds.

To evaluate the diversity of a selected set of compounds, the similarity between each pair of compounds of the set can be evaluated using the similarity calculations described above. For N compounds, an N×N matrix can be constructed where each element is a similarity measure. Actually, only the portion of the matrix above or below the diagonal is needed since the matrix has symmetry and the other half below (above) the diagonal is not needed when a symmetric similarity measure is employed.

The matrix elements with the highest values signify pairs of compounds such that one is a candidate for replacement. A new compound can be evaluated to replace a compound of the original pair. This new compound can be selected, for example, from the same cluster as the old compound. The new compound can replace the old compound if its similarity measure with the other compounds indicates that it is a better choice. The evaluation can be based on the maximum values, a root mean square average of the similarity measure against all of the other compounds or some other criteria.

An alternative approach can be used to select a diverse set of compounds from a large group of compounds. First, the structural and property descriptors are calculated for a large group of molecules. The computed values can be ordered, for example using the Topological Data Assembler described above. Then, a desired number of compounds N are selected from different bins for the first descriptor. If two or more molecules fall into the same bin for the second descriptor, all except one are thrown out. Another compound from the bin for the first descriptor of the thrown out molecule is selected and examined with respect to its second descriptor. The process is repeated until the molecules are all from different bins for all of the descriptors that the user deems important.

Both of these approaches for diversity planning are useful for selecting diverse compounds from a set of compounds to be evaluated. The two approaches can be combined as desired. The above procedures for diversity planning can be varied in a variety of ways based on the teachings above, as desired.

The selection and acquisition of a new database can be aided by an evaluation of its relationship to existing databases. Preferably, the new database has minimal overlap in diversity space relative to existing databases. The structural descriptors and property descriptors of the present approach provides a useful quantitative framework for such an evaluation. The evaluation can be performed by first calculating the structural and property descriptors for the molecules in the databases. The results are organized for each database, for example, as described using the Topological Data Assembler of FIG. 4.

For each descriptor deemed important, the range of parameters in the bins is examined to evaluate the amount of overlap in that parameter between the database in question and the existing databases. The values in the bins of the database under question should not be well represented in the existing databases, thus indicating that the databases are complementary. If several databases are evaluated against existing databases, the best new database can be selected based on better complementarity with respect to the existing databases, i.e., less overlap.

The discussion of particular embodiments above is intended to be representative and not limiting. Additional embodiments of the invention are within the claims.

What is claimed is:

1. A method of classifying molecules for assisting with the selection of chemical compounds for further study, said method comprising:
    (a) forming a 3-dimensional body representative of structure of said molecule by placing a potentially overlapping ball around each atom or group of atoms of said molecule, said ball having a radius selected for the particular type of atom or group of atoms;
    (b) generating structural descriptors reflecting structural information about neighboring atomic centers or groups of atomic centers of said molecule, said structural descriptors relating to a Voronoi diagram corresponding to said 3-dimensional body; and
    (c) classifying said molecule using said descriptors by identifying values associated with said descriptors.

2. The method of claim 1, wherein said descriptors are obtained by performing a weighted Delaunay triangulation to obtain topological elements associated with said molecular structure.

3. The method of claim 2, wherein said topological elements are selected from the group consisting of a vertices, edges, triangles, tetrahedrons and combinations thereof.

4. The method of claim 2, wherein an additional descriptor is associated with each atom or group of atoms.

5. The method of claim 4, wherein said additional descriptor relates to a property selected from the group consisting of polarity, hydrophobicity, hydrophilicity, chemical reactivity, location relative to the surface of said molecule, location relative to the convex hull of the 3-dimensional body, local concavity of the surface of said molecule and relationship to cavities.

6. The method of claim 4, wherein said additional descriptor is selected from the group consisting of the characteristic alpha value of said structural descriptors, a star relation and a link relation.

7. An electronic storage device comprising a storage medium, where said storage medium stores a computer program for implementing said classification method of claim 2.

8. A method of identifying molecules that are similar to a known compound comprising the steps of:
(a) classifying said known compound based on a classification method of claim 2;
(b) identifying significant elements within said classification method in terms of classification parameters;
(c) determining classifications of relevant molecules having the identified classification parameters similar or identical with said known compound; and
(d) establishing the structure of a molecule corresponding to said determined classifications of relevant molecules.

9. The method of claim 8, further comprising the step of evaluating the chemical properties of a chemical compound corresponding to said established structure.

10. A method of evaluating the degree of similarity between two molecules comprising the steps of:
(a) classifying said two molecules based on the classification method of claim 2; and
(b) determining the degree of similarity between said two molecules based on a comparison of said descriptors determined for each of said two molecules.

11. A method of selecting a diverse group of compounds for evaluation of efficacy from a collection of relevant molecules, said method comprising the steps of:
(a) classifying a set of compounds, using the classification method of claim 2;
(b) identifying significant elements within said classification method in terms of classification parameters; and
(c) selecting based on said classification parameters a diverse set of compounds within said evaluated set of compounds.

12. A method of selecting and evaluating the efficacy of a chemical compound, said method comprising the steps of:
(a) classifying a known compound based on the classification method of claim 2;
(b) identifying a compound from a group of compounds having a similar classification, with respect to significant features, to said known compound based on the same classification method used in step (a); and
(c) evaluating efficacy of said identified molecule using a chemical or pharmacological test.

13. A method of classifying molecules for assisting with the selection of chemical compounds for further study, said method comprising:
(a) performing a Delaunay triangulation based on a 3-dimensional body representative of structure of said molecule, wherein the three dimensional body is associated with the structure of said molecule based on the atomic centers of the molecular structure constructed with selected atomic radii, to obtain a set of topological elements including, at least, triangles and tetrahedra;
(b) classifying said molecule based on these topological elements by identifying values associated with said topological elements.

14. The method of claim 13, wherein an additional descriptor is associated with each atom.

15. The method of claim 14, wherein said additional descriptor relates to a property selected from the group consisting of polarity, hydrophobicity, hydrophilicity, chemical reactivity, location relative to the surface of said molecule, location relative to the convex hull of the 3-dimensional body, local concavity of the surface of said molecule and relationship to cavities.

16. The method of claim 14, wherein said additional descriptor is selected from the group consisting of the characteristic alpha value of said structural descriptors, a star relation and a link relation.

17. An electronic storage device comprising a storage medium, where said storage medium stores a computer program for implementing said classification method of claim 13.

18. A method of identifying molecules that are similar to a known compound comprising the steps of:
(a) classifying said known compound based on a classification method of claim 13;
(b) identifying significant elements within said classification method in terms of classification parameters;
(c) determining classifications of relevant molecules having the identified classification parameters similar or identical with said known compound; and
(d) establishing the structure of a molecule corresponding to said determined classifications of relevant molecules.

19. The method of claim 18, further comprising the step of evaluating the chemical properties of a chemical compound corresponding to said established structure.

20. A method of selecting and evaluating the efficacy of a chemical compound, said method comprising the steps of:
(a) classifying a known compound based on the classification method of claim 13;
(b) identifying a compound from a group of compounds having a similar classification, with respect to significant features, to said known compound based on the same classification method used in step (a); and
(c) evaluating efficacy of said identified molecule using a chemical or pharmacological test.

* * * * *